US006037491A

United States Patent [19]
Vassiliou et al.

[11] Patent Number: 6,037,491
[45] Date of Patent: Mar. 14, 2000

[54] METHODS AND DEVICES FOR CONTROLLING HYDROCARBON OXIDATIONS TO RESPECTIVE ACIDS BY ADJUSTING THE SOLVENT TO HYDROCARBON RATIO

[75] Inventors: Eustathios Vassiliou, Newark, Del.; Mark W. Dassel, Indianola, Wash.; Sharon M. Aldrich, Poulsbo, Wash.; Ader M. Rostami, Bainbridge Island, Wash.; David C. DeCoster, Buckley, Wash.

[73] Assignee: RPC Inc., Atlanta, Ga.

[21] Appl. No.: 08/900,323

[22] Filed: Jul. 25, 1997

[51] Int. Cl.$^7$ .................................................. C07C 51/16
[52] U.S. Cl. ...................... 562/413; 562/512.4; 562/528; 562/538; 562/543; 562/529; 568/357; 568/358; 568/570; 568/836
[58] Field of Search ................................ 562/413, 512.4, 562/528, 538, 543, 529; 568/357, 358, 570, 836

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,223,493 | 12/1940 | Loder | 260/537 |
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,839,435 | 10/1974 | Shigeyasu et al. | 260/524 R |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,025,498 | 5/1977 | Buss et al. | 260/95 A |
| 4,032,569 | 6/1977 | Onopchenko et al. | 260/533 |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,158,739 | 6/1979 | Schulz et al. | 562/543 |
| 4,263,453 | 4/1981 | Schulz et al. | 562/543 |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 5,061,453 | 10/1991 | Krippl et al. | 422/106 |
| 5,104,492 | 4/1992 | King et al. | 203/15 |
| 5,117,007 | 5/1992 | Taheri | 549/259 |
| 5,123,936 | 6/1992 | Stone et al. | 55/8 |
| 5,170,727 | 12/1992 | Nielson | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,547,905 | 8/1996 | Kulsretha et al. . | |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,756,837 | 5/1998 | Costantini et al. | 562/543 |

FOREIGN PATENT DOCUMENTS

| | | |
|---|---|---|
| 439 007 A2 | 7/1991 | European Pat. Off. . |
| 729 084 A1 | 8/1996 | European Pat. Off. . |
| 729 085 A1 | 8/1996 | European Pat. Off. . |
| 751 105 A2 | 1/1997 | European Pat. Off. . |
| 2 722 783 A1 | 1/1996 | France . |

(List continued on next page.)

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+ English language translation).

*Primary Examiner*—Samuel Barts
*Attorney, Agent, or Firm*—Seed and Berry LLP

[57] ABSTRACT

This invention relates to methods and devices of preparing acids, such as adipic acid for example, by oxidizing a hydrocarbon, such as cyclohexane for example, with a gas containing an oxidant, preferably oxygen. A respective hydrocarbon is reacted, preferably at a steady state, with a gaseous oxidant to form an acid in a liquid mixture which preferably contains a solvent, a catalyst, water, and an initiator. The ratio of solvent to hydrocarbon may be controlled in a manner to maintain in the reaction zone maximum reaction rate and/or reactivity, or reaction rate and/or reactivity within a desired range, or reaction rate and/or reactivity directed toward a desired range. In addition, the ratio of solvent to hydrocarbon is controlled in a manner to maintain in the reaction zone substantially maximum selectivity and/or yield, or selectivity and/or yield within a desired range, or selectivity and/or yield directed toward a desired range.

30 Claims, 1 Drawing Sheet

FOREIGN PATENT DOCUMENTS

| | | |
|---|---|---|
| 4426132A1 | 1/1996 | Germany . |
| 61-063634 | 4/1986 | Japan . |
| 415172 | 8/1934 | United Kingdom . |
| 738808 | 10/1955 | United Kingdom . |
| 864106 | 3/1961 | United Kingdom . |
| 1143213 | 2/1969 | United Kingdom ........................ 51/16 |
| 2 014 473 | 8/1979 | United Kingdom . |
| WO96/03365 | 2/1996 | WIPO . |
| WO 96/40610 | 12/1996 | WIPO . |
| WO 97/49485 | 12/1997 | WIPO . |

METHODS AND DEVICES FOR CONTROLLING HYDROCARBON OXIDATIONS TO RESPECTIVE ACIDS BY ADJUSTING THE SOLVENT TO HYDROCARBON RATIO

FIELD OF THE INVENTION

This invention relates to methods and devices for oxidizing hydrocarbons, such as cyclohexane for example, to respective acids, such as adipic acid for example, by a direct process.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase". However, no attention has been paid so far to the importance of the two phases, except for separating the adipic acid from the "Polar Phase" and recycling these phases to the reactor partially or totally with or without further treatment.

It is also important to note that most studies on the Direct Oxidation have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and intermediate products.

U.S. Pat. No. 5,463,119 (Kollar) discloses a process for the oxidative preparation of $C_5$–$C_8$ aliphatic dibasic acids by (1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al) discloses formation of cyclohexyladipates in a staged reactor, e.g., a reactive distillation column. A mixture containing a major amount of benzene and a minor amount of cyclohexane is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the C5–C8 aliphatic dibasic acid.

U.S. Pat. No. 5,221,800 (Park et al) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of eyelohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,390,174 (Schultz et al) discloses a process claiming improved yields of aliphatic dibasic acids when oxidizing the respective cyclic hydrocarbons at temperatures between 130° and 160° C., while removing the water of reaction substantially as quickly as it is formed.

U.S. Pat. No. 3,361,806 (Lidov et al) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Ilamblet et al) discloses production of adipic acid and related aliphatic dibasic acids; more particularly to the production of adipic acid by the direct oxidation of cyclohexane.

U.S. Pat. No. 2,439,513 (Hamblet et al) discloses the production of adipic acid and related aliphatic dibasic acids and more particularly to the production of adipic acid by the oxidation of cyclohexane.

U.S. Pat. No. 2,223,494 (Loder et al) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

None of the above references, or any other references known to the inventors disclose, suggest or imply, singly or in combination, control of oxidation reactions by adjusting the solvent to hydrocarbon ratio subject to the intricate and critical controls and requirements of the instant invention as described and claimed.

Our U.S. Pat. Nos. 5,580,531, 5,558,842, 5,502,245, and our co-pending applications Ser. No. 08/477,195 (filed Jun. 7, 1995), 08/587,967 (filed Jan. 17, 1996), and 08/620,974 (filed Mar. 25, 1996), all of which are incorporated herein by reference, describe methods and apparatuses relative to controlling reactions in atomized liquids. Our co-pending application, Docket No. T-603, Ser. No. 08/812847, filed on Mar. 6, 1997, and our co-pending application, Docket No. T-701, Ser. No. 08/824992, filed on Mar. 27, 1997 are both also incorporated herein by reference.

All of the following patent applications, which were filed simultaneously on May 21, 1997, are also incorporated herein by reference:

U.S. Pat. application Ser. No. 08/859,985 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments";

U.S. Pat. application Ser. No. 08/861,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

U.S. Pat. application Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a RateModulator";

U.S. Pat. application Ser. No. 08/861,176 of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator";

U.S. Pat. application Ser. No. 08/859,890 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements"; and U.S. Pat. application Ser. No. 08/861,210 of Eustathios Vassiliou, Ader M. Rostami, David C. DeCoster, and Mark W. Dassel, titled "Pseudo-Plug-Flow Reactor".

Further, our patent application having U.S. Pat. application Ser. No. 08/876,692, filed on Jun. 16, 1997, of Ader M. Rostami, David C. DeCoster, Eustathios Vassiliou, Mark W. Dassel, and Sharon M. Aldrich, titled "Methods and Devices for Controlling Hydrocarbon Oxidations to Respective Acids by Adjusting the Water Level during the Reaction" is also incorporated herein by reference.

In addition, our PCT patent application having International application No. PCT/US 97112944 filed on Jun. 23, 1996 of David C. DeCoster, Eustathios Vassiliou, Mark W. Dassel, Sharon M. Aldrich, and Ader M. Rostami, titled "Methods and Devices for Controlling the Reaction Rate and/or Reactivity of Hydrocarbon to an Intermediate Oxidation Product by Adjusting the Oxidant Consumption Rate" is also incorporated herein by reference.

SUMMARY OF THE INVENTION

As aforementioned, this invention relates to methods and devices for oxidizing hydrocarbons, such as cyclohexane for example, to respective acids, such as adipic acid for example, by a direct process. Particularly, it pertains a method of controlling in a reaction zone the oxidation of a hydrocarbon to form a respective acid in a liquid mixture comprising catalyst, solvent, water, and optionally initiator, the solvent and the hydrocarbon having an initial solvent to hydrocarbon ratio, at desired levels of catalyst, water, and initiator, the method being characterized by the steps:

(a) contacting the liquid mixture with a gaseous oxidant in the reaction zone at a first temperature, the first temperature being adequately high for the oxidation to proceed;

(b) controlling the solvent to hydrocarbon ratio within a range at which reaction rate and/or reactivity is substantially maximized at the desired levels of catalyst, water, and initiator.

It is important that the liquid mixture is maintained as a single liquid phase at the first temperature.

Reaction rate is defined as the molar oxidation of hydrocarbon per unit of time.

Reactivity is defined as the reaction rate divided by the total volume of mixture involved in a reaction; in other words the reactivity per unit volume of mixture involved in the reaction.

The term "solvent to hydrocarbon ratio" in a continuous operation is defined as the weight ratio of solvent to hydrocarbon at the exit or outlet line of a reaction zone, as it will also be explained later. This is substantially the same ratio as the solvent to hydrocarbon ratio in the reaction chamber at a steady state.

By the term "steady state" it is meant that the reaction has reached an equilibrium, which equilibrium, however, may be adjusted periodically or continuously in order to achieve a desired result.

The term "level" of an ingredient (reactant, reaction product, inert matter, or any other type of matter present) includes both "relative level" and "percentage level". According to the instant invention, both methods and devices may perform by using either one or the other type of "levels". In some occasions it may be easier to use one type rather than the other. "Relative level" of an ingredient denotes the amount of the ingredient present in weight units or in volume units, in a reaction zone, as compared to 100 units, in weight units or in volume units, respectively, of the rest of the ingredients present, or the rest of the ingredients under consideration. On the other hand, "percentage level" is the level expressed as a percentage based on total amount of all or of a desired number of specific ingredients. The percentages may be expressed also either by weight or by volume.

Controlling the solvent to hydrocarbon ratio may comprise, in one embodiment of the present invention, a step of initially increasing the solvent to hydrocarbon ratio by a predetermined increment, and (a) if the reaction rate and/or reactivity increases, continuing to increase the solvent to hydrocarbon ratio to a point that no further increase in reaction rate and/or reactivity is realized; and (b) if the reaction rate and/or reactivity decreases, lowering the solvent to hydrocarbon ratio, and if the reaction rate and/or reactivity increases, continuing to decrease the solvent to hydrocarbon ratio to a point that no further increase in reaction rate and/or reactivity is realized.

Controlling the solvent to hydrocarbon ratio may comprise, in a different embodiment of this invention, a step of initially decreasing the solvent to hydrocarbon ratio by a predetermined increment, and (a) if the reaction rate and/or reactivity increases, continuing to decrease the solvent to hydrocarbon ratio to a point that no further increase in reaction rate and/or reactivity is realized;

(b) if the reaction rate and/or reactivity decreases, increase the solvent to hydrocarbon ratio, and if the reaction rate and/or reactivity increases, continuing to increase the solvent to hydrocarbon ratio to a point that no further increase in reaction rate and/or reactivity is realized.

If increasing or decreasing the solvent to hydrocarbon ratio by a predetermined increment, does not change the reaction rate and/or reactivity, the solvent to hydrocarbon ratio should preferably be maintained substantially at its initial value.

This invention also relates to a method of controlling in a reaction zone the oxidation of a hydrocarbon to form a respective acid in a liquid mixture comprising catalyst, solvent, water, and optionally initiator, the solvent and the hydrocarbon having an initial solvent to hydrocarbon ratio, at desired levels of catalyst, water, and initiator, the method being characterized by the steps:

(a) contacting the liquid mixture with a gaseous oxidant in the reaction zone at a first temperature, the first temperature being adequately high for the oxidation to proceed; and (b) controlling the solvent to hydrocarbon ratio in a manner that reaction rate and/or reactivity is substantially maintained within a desired reaction rate and/or reactivity range, or in a manner that the reaction rate and/or reactivity is directed toward said reaction rate and/or reactivity range if the reaction rate and/or reactivity is outside the desired reaction rate and/or reactivity range at the initial solvent to hydrocarbon ratio, at the desired levels of catalyst, water, and initiator.

Controlling the solvent to hydrocarbon ratio may comprise a step of initially increasing the solvent to hydrocarbon ratio by a predetermined increment, and (a) if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and (b) if the reaction rate and/or reactivity moves away from the desired reaction rate and/or reactivity range, lowering the solvent to hydrocarbon ratio, and if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

Alternatively, controlling the solvent to hydrocarbon ratio may comprise a step of initially decreasing the solvent to hydrocarbon ratio by a predetermined increment, and (a) if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and (b) if the reaction rate and/or reactivity moves away from the desired reaction rate and/or reactivity range, increasing the solvent to hydrocarbon ratio, and if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

If the reaction rate and/or reactivity is within the desired reaction rate and/or reactivity range, the solvent to hydrocarbon ratio should preferably be maintained substantially at its initial value.

For further increasing reaction rate and/or reactivity, the liquid mixture may be at least partially atomized.

In a preferred embodiment of this invention, the hydrocarbon comprises a compound selected from a group consisting of cyclohexane, cyclohexanone, cyclohexanol, cyclohexylhydroperoxide, o-xylene, m-xylene, and p-xylene; the oxidant comprises oxygen; and a major portion of the acid comprises a compound selected from a group consisting of adipic acid, phthalic acid, isophthalic acid, and terephthalic acid.

The methods of the present invention may also utilize the control of solvent to hydrocarbon ratio in a manner to direct the oxidation of the hydrocarbon toward a preferred range or value of selectivity and/or yield, or to maintain the oxidation of the hydrocarbon within a preferred range of selectivity and/or yield, instead of, or in addition to controlling reaction rate and/or reactivity and/or reaction rate, by using substantially the same techniques.

According to this invention, selectivity, such as acid selectivity for example, is defined as the mole percent of desired acid formed based on total acid. For example, in the case of adipic acid formation, the acid is calculated by dividing the number of moles of adipic acid formed in the reaction by the moles of all acids formed (typically adipic, glutaric and succinic), and by multiplying by 100.

Yield is defined as the actual number of moles of a desired product formed, divided by the moles of the desired product that should have been formed theoretically, and multiplied by 100.

This invention is particularly suited in the case wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

It is highly preferable that the liquid mixture during the reaction, and at the operation temperature, has substantially only one liquid phase in the presence or absence of a solid and/or gaseous phase. Presence of a second liquid phase lowers the reaction rate and/or reactivity considerably.

Further, the instant invention pcitainis to a method, wherein the intermediate oxidation product comprises a compound selected from a group consisting of adipic acid, phthalic acid, isophthalic acid, and terephithalic acid, and the method further comprises a step of reacting said intermediate oxidation product with a third reactant selected from a group consisting of a polyol, a polyamine, and a polyamide in a manner to form a polymer of a polyester, or a polyamilde, or a (polyimide and/or polyamideimide), respectively.

The method may further comprise a step of spinning the polymer into fibers.

The instant invention also pertains a reactor device for controllably oxidizing a hydrocarbon with a gaseous oxidant to form a respective acid in the presence of a solvent, a catalyst, and an optional initiator, the device being characterized by:

a reaction chamber;

feeding means connected to the reaction chamber for feeding gaseous oxidant, solvent, hydrocarbon, catalyst, and optional initiator into the reaction chamber; and control means connected to the feeding means for adjusting feeding or flow rates of the hydrocarbon and solvent into the reaction chamber in a manner to direct said flows toward a desired solvent to hydrocarbon ratio, which desired ratio yields substantially maximum reaction rate and/or reactivity.

The reactor device may further comprise reaction rate and/or reactivity determining means connected to the reaction chamber for determining reaction rate and/or reactivity in the reaction chamber.

The reactor device may comprise an atomization reactor, or a stirred-tank reactor, or a recirculation reactor, or a combination thereof, or any other type of reactor.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

Figure 1:
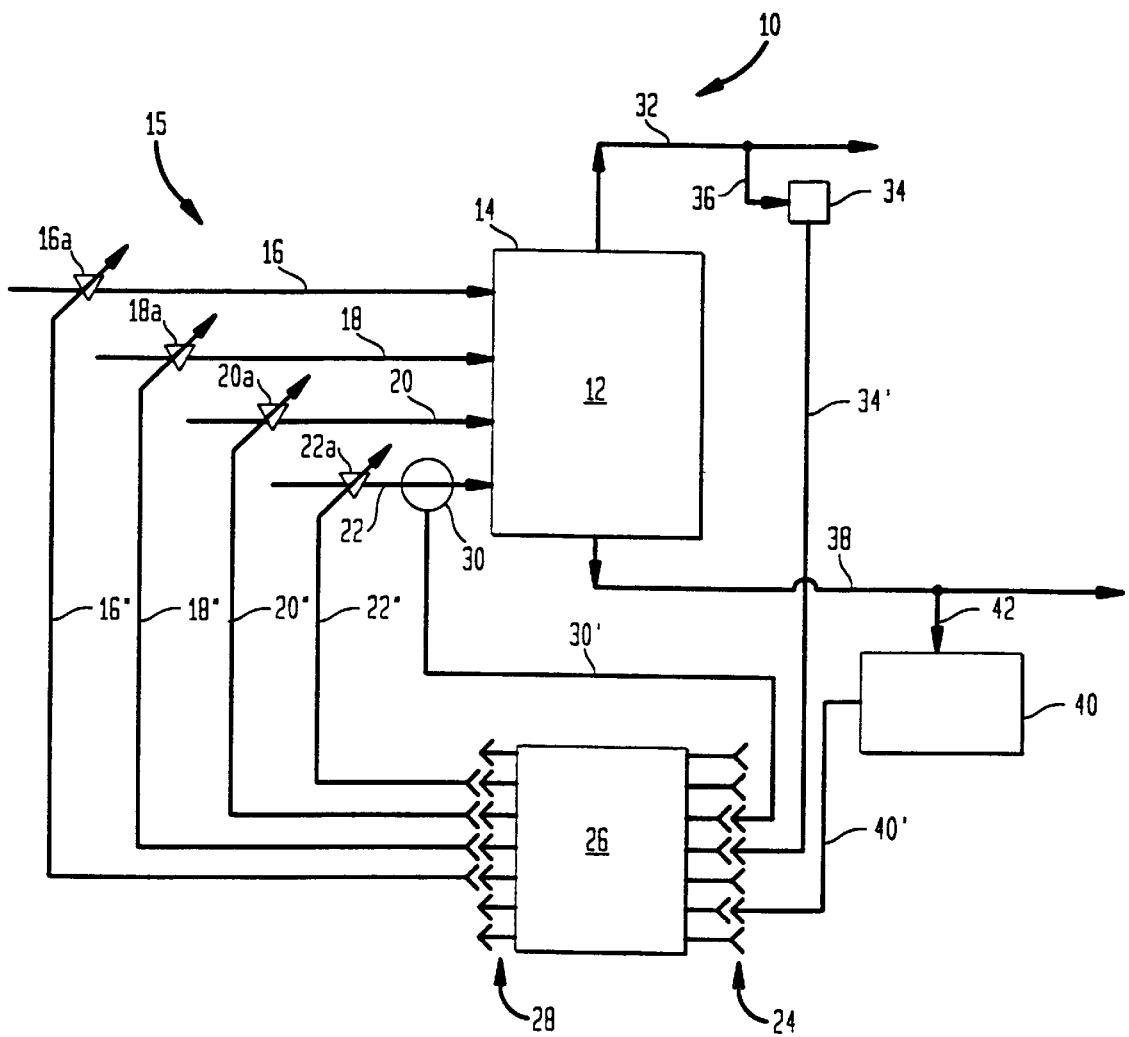
FIG. 1 illustrates a simplified block diagram of preferred embodiments of the present invention.

As aforementioned, this invention relates to methods and devices for oxidizing hydrocarbons, such as cyclohexane for example, to respective acids, such as adipic acid for example, by a direct process.

Reaction rate, and more particularly reactivity, as earlier defined, are extremely important parameters, since they may render any particular process or device economically feasible. Even in an extreme case, wherein the conversion is 100%, and the yield is 100%, if the reactivity is unacceptably low, the process becomes necessarily uneconomical.

According to this invention, the reaction rate and/or reactivity of a hydrocarbon to form an acid may be maximized by controlling the solvent to hydrocarbon ratio.

However, although it is highly preferable that the reaction rate and/or reactivity is maximized, there are circumstances, under which it is desirable for the reaction rate and/or reactivity to assume a value lower than the maximum value, if the conversion, selectivity, yield, etc., counterbalance and overcome any benefits obtained by the maximization of the reaction rate and/or reactivity. In such circumstances, the solvent to hydrocarbon ratio is maintained at such levels which control the reaction rate and/or reactivity to be within a desired reaction rate and/or reactivity range, lower than the maximum reaction rate and/or reactivity.

According to this invention the solvent to hydrocarbon ratio may be controlled in a manner that the selectivity and/or yield are either maximized, or directed toward a desired range of selectivity and/or yield, or are maintained within a desired range of selectivity and/or yield. The examples below refer mainly to reaction rate and/or reactivity, but they apply equally well to selectivity and/or yield.

This invention may be exemplified by referring to FIG. 1. In FIG. 1, there is depicted a reactor system or device 10, comprising a reaction chamber 12 containing a reaction zone 14. The reactor system 10 is only partially shown for demonstrating the components necessary to clearly exemplify the present invention. Miscellaneous treatment, product or by-product separation, recycling, etc. devices, well known to the art, are not shown for purposes of clarity and brevity.

The reaction chamber 12 may be a stirred-tank reactor, atomization reactor, re-circulation reactor, or any other type of reactor, known to the art.

A number of feed lines, being at least part of feeding means 15, such as general feed line 16, solvent feed line 18, hydrocarbon feed line 20, and gaseous oxidant feed line 22 are shown to be connected to the reaction chamber 12. These feed lines have been illustrated in this manner in order to better exemplify and demonstrate the present invention. However, these lines may be combined, they may include recirculated matter, they may be multiple or single lines, etc. The feeding means 15 may also include heat exchangers, pre-mixing vessels, flowmeters, thermocouples, etc., and they are connected (not shown for purposes of clarity and brevity) to one or more of inputs 24 of a controller 26. In turn the controller 26 is connected to the liquid feeding means 15, through one or more of its outputs 28, and controls its operation by methods well known to the art.

Valves 16a, 18a, 20a, and 22a, are connected to lines 16, 18, 20, and 22 respectively, controlling the flow rate of respective matter passing through these lines into the reaction zone 14 of the reaction chamber 12. These valves are controlled by the output lines 16", 18", 20", and 22" of the controller 26, respectively.

A flowmeter 30 is connected to line 22 for monitoring the flow of the gaseous oxidant passing through line 22 into the reaction zone 14 of the reaction chamber 12. Flow rate information is provided to the controller 26 through input line 30', which is connected to one of inputs 24 of the controller 26. Flow meters and other devices giving information to the controller 26 from lines 16, 18, and 20 are not shown for purposes of clarity. For the same reason of clarity and brevity, temperature and pressure monitors, as well as means to control the temperature and pressure in the reaction zone 14 of the reaction chamber 12 are not shown, but they are very well known to the art.

An off-gas outlet line 32 is connected to the reaction chamber 12 for removing the off-gases. Reflux condensers, decanters, distillation columns, or other such devices, well known to the art, useful in the process of heat balance and/or recirculation of matter are not shown for purposes of clarity.

An oxygen analyzer 34 may be connected to the off-gas outlet 32 through a first sampling line 36, for analyzing the content of oxygen in the off-gases. The oxygen content information is provided to controller 26 though input line 34', which is connected to one of the inputs 24 of the controller 26.

Matter reacted in the reaction zone 14 of the reaction chamber 12 is removed through outlet line 38 for further treatment, separation of products of oxidation, recirculation, etc.

An analyzer 40 may be connected to the outlet line 38 through a second sampling line 42, for analyzing the stream passing through the outlet line 38, especially for its content in hydrocarbon, such as cyclohexane for example, as far as this invention is concerned. Of course, the analyzer 40 may analyze the stream for any other of its constituents, including but not limited to solvent, water, oxidation products, such as adipic acid for example, by-products, such as succinic and glutaric acids for example, etc. The analyzer 40 may preferably comprise analytical instrumentation, such as HPLC, GC, GC/MS, GC/FID, for example, and the like. The analytical information is in turn provided to the controller 26 through input line 40', which is connected to one of the inputs 24 of the controller 26.

In operation of this embodiment, preferably under steady state conditions, hydrocarbon, such as cyclohexane for example, is fed to the reaction zone 14 of the reaction chamber 12 through line 20, while solvent is fed through line 18, and oxygen is fed through line 22. Catalyst, optionally water, and optionally initiator are fed through line 16. As aforementioned, lines 16, 18 and 20 are shown as separate lines for better exemplifying this invention, although other materials may be present in these lines, such as for example mixtures of one or more of solvent, hydrocarbon, catalyst, water initiator, etc., in miscellaneous proportions. The controller may either calculate the composition of each stream passing through lines 16, 18, and 20 based at least partially on information from material balance data, or obtain compositional determinations from additional analyzers (not shown) included in the feeding means 15 or elsewhere. For purposes of simplicity, it is assumed momentarily that all the solvent is fed through line 18, and all of the hydrocarbon is fed through line 20.

The reaction rate and reactivity may be determined by the controller 26 by a number of different ways. Information obtained from flowmeter 30 gives the flow rate of the incoming oxidant, such as oxygen for example, while information provided by the oxygen analyzer 34 relates to the flow rate of outgoing oxidant. The flow rate difference between incoming and outgoing oxidant is a practical measure of the reaction rate. The reactivity may be calculated by taking into account the volume of nongaseous matter inside the reaction chamber 12.

A more accurate way of determining the reaction rate is from the difference of the flow rate of incoming hydrocarbon, from line 20 for example (assuming for simplicity purposes that the totality of hydrocarbon enters the reaction chamber 12 through line 20), and the flow rate of hydrocarbon exiting the reaction chamber 12 through line 38, as determined by the analyzer 40. The reactivity in this case also may be calculated by taking into account the volume of non-gaseous matter inside the reaction chamber 12.

Other methods of determining the reaction rate and/or reactivity are explained in detail in our aforementioned patent applications, having U.S. application Ser. Nos. 08/859,985 and 08/861,281 which have been incorporated herein by reference.

As aforementioned, the term "solvent to hydrocarbon ratio" in a continuous operation is defined as the weight ratio of solvent to hydrocarbon at the exit or outlet line of a reaction zone. This is substantially the same as, or at least very close to the solvent to hydrocarbon ratio inside the reaction zone 14 of the reaction chamber 12. Such an outlet line is line 38. The analyzer 40 samples the stream in line 38 through sampling line 42, for both solvent and hydrocarbon content, from which the ratio of solvent to hydrocarbon is derived. In the case of batch operation, the solvent to hydrocarbon ratio changes continuously, and it cannot be controlled easily.

In sequence, during the operation of this embodiment, the flow rate of incoming solvent though line 18 (assuming again for purposes of simplicity that the only solvent entering the reaction zone 14 passes through line 18) is increased by a predetermined increment, and the flow rate of hydrocarbon 20 is decreased by a respective increment, so that the total mass of solvent and hydrocarbon entering the reaction zone 14 remains constant. This changes the ratio of solvent to hydrocarbon entering the reaction zone 14 also by a respective predetermined increment.

If the reaction rate and/or reactivity increases, then the solvent to hydrocarbon ratio is further increased, preferably incrementally, until no further increase in reaction rate and/or reactivity is realized. If the reaction rate and/or reactivity decreases by increasing the solvent to hydrocarbon ratio, the solvent to hydrocarbon ratio is lowered to a point lower than the initial solvent to hydrocarbon ratio. If by this action, the reaction rate and/or reactivity increases, the solvent to hydrocarbon ratio is further lowered until no further increase in reaction rate and/or reactivity is realized.

Alternatively (assuming again for purposes of simplicity that the only solvent entering the reaction zone 14 passes through line 18), the operation may start with decreasing the solvent to hydrocarbon ratio by a predetermined increment, and increasing the flow rate of hydrocarbon by a respective increment, so that the total mass of solvent and hydrocarbon entering the reaction zone 14, through lines 18 and 20 respectively, remains constant. This changes the ratio of solvent to hydrocarbon entering the reaction zone 14 also by a respective predetermined increment.

If the reaction rate and/or reactivity increases, then the solvent to hydrocarbon ratio is further decreased, preferably incrementally, until no further increase in reaction rate and/or reactivity is realized. If the reaction rate and/or reactivity decreases by decreasing the solvent to hydrocarbon ratio, the solvent to hydrocarbon ratio is raised to a point higher than the initial solvent to hydrocarbon ratio. If by this action, the reaction rate and/or reactivity increases, the solvent to hydrocarbon ratio is further raised until no further increase in reaction rate and/or reactivity is realized.

If increasing or decreasing the solvent to hydrocarbon ratio by a predetermined increment, does not change the reaction rate and/or reactivity, the solvent to hydrocarbon ratio is maintained substantially at its initial value.

In many cases, it is desirable to maintain the reaction rate and/or reactivity within a predetermined range, instead of maximizing it. In such occasions, the operation is similar to that described hereinbelow.

The solvent flow rate may be initially increased by a predetermined increment so that the solvent to hydrocarbon ratio is also increased from its initial value by a respective predetermined increment. If the reaction rate and/or reactivity moves toward the desired reaction rate and/or reactivity range, the solvent to hydrocarbon ratio is further increased, preferably incrementally, to a point that the reaction rate and/or reactivity falls within said desired reaction rate and/or reactivity range.

If the reaction rate and/or reactivity moves away from the desired reaction rate and/or reactivity range, the solvent to hydrocarbon ratio is lowered, and if the reaction rate and/or reactivity moves toward the desired reaction rate and/or reactivity range, the solvent to hydrocarbon ratio is further decreased, preferably incrementally, to a point that the reaction rate and/or reactivity falls within the desired reaction rate and/or reactivity range.

Alternatively, the solvent to hydrocarbon ratio may be initially decreased by a predetermined increment. If the reaction rate and/or reactivity moves toward the desired reaction rate and/or reactivity range, the solvent to hydrocarbon ratio is further decreased to a point that the reaction rate and/or reactivity falls within said desired reaction rate and/or reactivity range. If the reaction rate and/or reactivity moves away from the desired reaction rate and/or reactivity range, the solvent to hydrocarbon ratio is increased. If the reaction rate and/or reactivity moves toward the desired reaction rate and/or reactivity range, the solvent to hydrocarbon ratio is further increased to a point that the reaction rate and/or reactivity falls within said desired reaction rate and/or reactivity range.

If the reaction rate and/or reactivity is within the desired reaction rate and/or reactivity range, the solvent to hydrocarbon ratio is substantially maintained at its initial value.

The increments for changing the flow rate of incoming solvent (with respective changes in incoming hydrocarbon) are preferably smaller than 15%, more preferably smaller than 10%, and even more preferably in the range of 2–7%. Thus, for example, if the initial flow rate of solvent is 60 units and the flow rate of hydrocarbon is 40 units, the incremental changes in flow of solvent are preferably smaller than 9 units, more preferably smaller than 6 units, and even more preferably, in the range of 1.2 to 4.2 units. The respective changes in hydrocarbon flow rate should be such that the sum of the solvent units and the hydrocarbon units is substantially equal to a total of 100 flow rate units.

The frequency and response of incremental changes depend on the size of the reaction zone 14 within the reaction chamber 12, the flow rates, and other parameters in each individual case. However, they can be determined easily for the individual circumstances.

The methods and devices of the present invention may utilize the control of solvent to hydrocarbon ratio in a manner to direct the oxidation of the hydrocarbon toward a preferred range or value of selectivity and/or yield, or to maintain the oxidation of the hydrocarbon within a preferred range of selectivity and/or yield, instead of, or in addition to controlling reactivity and/or reaction rate, by using substantially the same techniques.

It is highly preferable that during this operation of adjusting the solvent to hydrocarbon ratio, the levels of catalyst, optional initiator, and water in the reaction zone 14 of the reaction chamber 12 remain substantially constant. If they are changed for any reason at all, a new adjustment of the solvent to hydrocarbon ratio would be appropriate. As aforementioned, in the above examples it is assumed, just for purposes of better demonstrating this invention, that the only solvent and hydrocarbon entering the reaction zone 14, come through lines 18 and 20, respectively, while other ingredients enter the reaction zone 14 though line 16, and the gaseous oxidant enters the reaction zone 14 through line 22. In practice, this is not usually the case. However, the controller 26 may control the streams of the miscellaneous lines in a manner to accomplish the same final result.

It should be understood that according to the present invention, any liquids or gases or off-gases may be recycled totally or partially from any section to any other section.

A preferable type of controller is a computerized controller. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be at each instance. The expert systems are programmed based on the expertise of experienced human beings. The fuzzy logic systems are based on intuition rules in addition to expertise rules.

Although the miscellaneous functions are preferably controlled by a computerized controller, it is possible, according to this invention, to utilize any other type of controller or even manual controls and/or labor for controlling one or more functions.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane. Examples of aromatic carboxylic acids are benzoic acid, phthalic acid, isophthalic acid, and terephthalic acid, among others.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyaminie, and the polyamide are mainly a diol, a diaminie, and a diamide, respectively, in order to avoid excessive cross-linking. The polymer resulting, from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention.

All explanations given hereinabove are to be considered as speculative and should not be construed as limiting the breadth of the claims.

All percentages and ratios are given by weight, unless otherwise defined.

What is claimed is:

1. A method of controlling in a reaction zone the oxidation of a hydrocarbon to form a respective acid in a liquid mixture comprising catalyst, solvent, water, and optionally initiator, the solvent and the hydrocarbon having an initial solvent to hydrocarbon ratio, at desired levels of catalyst, water, and initiator, the method being characterized by the steps:

(a) contacting the liquid mixture with a gaseous oxidant in the reaction zone at a first temperature, the first temperature being adequately high for the oxidation to proceed;

(b) maintaining the liquid mixture in a single liquid phase at the first temperature; and (c) controlling the solvent to hydrocarbon ratio in a manner that reaction rate and/or reactivity is substantially maintained within a desired reaction rate and/or reactivity range, or in a manner that the reaction rate and/or reactivity is directed toward said reaction rate and/or reactivity range if the reaction rate and/or reactivity is outside the desired reaction rate and/or reactivity range at the initial solvent to hydrocarbon ratio, at the desired levels of catalyst, water, and initiator.

2. A method as defined in claim 1 wherein controlling the solvent to hydrocarbon ratio comprises a step of initially increasing the solvent to hydrocarbon ratio by a predetermined increment, and (a) if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and (b) if the reaction rate and/or reactivity moves away from the desired reaction rate and/or reactivity range, lowering the solvent to hydrocarbon ratio, and if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

3. A method as defined in claim 1 wherein controlling the solvent to hydrocarbon ratio comprises a step of initially decreasing the solvent to hydrocarbon ratio by a predetermined increment, and (a) if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and (b) if the reaction rate and/or reactivity moves away from the desired reaction rate and/or reactivity range, increasing the solvent to hydrocarbon ratio, and if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

4. A method as defined in claim 1 wherein, if the reaction rate and/or reactivity is within the desired reaction rate and/or reactivity range, maintaining the solvent to hydrocarbon ratio substantially at its initial value.

5. A method as defined in claim 1 wherein the hydrocarbon comprises a compound selected from a group consisting of cyclohexane, cyclohexanone, cyclohexanol, cyclohexylhydroperoxide, o-xylene, m-xylene, and p-xylene;

the oxidant comprises oxygen; and a major portion of the acid comprises a compound selected from a group consisting of adipic acid, phthalic acid, isophthalic acid, and terephthalic acid.

6. A method as defined in claim 1 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

7. A method as defined in claim 2 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

8. A method as defined in claim 3 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

9. A method as defined in claim 4 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

10. A method as defined in claim 5 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

11. A method of preparing a polymer comprising the steps of:

(a) controlling in a reaction zone the oxidation of a hydrocarbon to form a respective dibasic acid selected from a group consisting substantially of adipic acid, phthalic acid, isophthalic acid, and terephthalic acid, in a liquid mixture comprising catalyst, solvent, water, and optionally initiator, the solvent and the hydrocarbon having an initial solvent to hydrocarbon ratio, at desired levels of catalyst, water, and initiator, the step of controlling the oxidation comprising sub-steps of:

contacting the liquid mixture with a gaseous oxidant in the reaction zone at a first temperature, the first temperature being adequately high for the oxidation to proceed, maintaining the liquid mixture in a single liquid phase at the first temperature; and controlling the solvent to hydrocarbon ratio in a manner that reaction rate and/or reactivity is substantially maintained within a desired reaction rate and/or reactivity range, or in a manner that the reaction rate and/or reactivity is directed toward said reaction rate and/or reactivity range if the reaction rate and/or reactivity is outside the desired reaction rate and/or reactivity range at the initial solvent to hydrocarbon ratio, at the desired levels of catalyst, water, and initiator; and (b) reacting said dibasic acid with a reactant selected from a group consisting of a polyol, a polyamine, and a polyamide in a manner to form a polymer of a polyester, or a polyamide, or a (polyimide and/or polyamideimide), respectively.

12. A method as defined in claim 11, further comprising a step of spinning the polymer into fibers.

13. A method as defined in claim 11 wherein controlling the solvent to hydrocarbon ratio comprises a step of initially increasing the solvent to hydrocarbon ratio by a predetermined increment, and (a) if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and (b) if the reaction rate and/or reactivity moves away from the desired reaction rate and/or reactivity range, lowering the solvent to hydrocarbon ratio, and if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

14. A method as defined in claim 11 wherein controlling the solvent to hydrocarbon ratio comprises a step of initially decreasing the solvent to hydrocarbon ratio by a predetermined increment, and
   (a) if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and
   (b) if the reaction rate and/or reactivity moves away from the desired reaction rate and/or reactivity range, increasing the solvent to hydrocarbon ratio, and if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

15. A method as defined in claim 11 wherein, if the reaction rate and/or reactivity is within the desired reaction rate and/or reactivity range, maintaining the solvent to hydrocarbon ratio substantially at its initial value.

16. A method as defined in claim 11 wherein the hydrocarbon comprises a compound selected from a group consisting of cyclohexane, cyclohexanone, cyclohexanol, cyclohexylhydroperoxide, o-xylene, m-xylene, and p-xylene;
   the oxidant comprises oxygen; and
   a major portion of the acid comprises a compound selected from a group consisting of adipic acid, phthalic acid, isophthalic acid, and terephthalic acid.

17. A method as defined in claim 11 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

18. A method as defined in claim 13 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

19. A method as defined in claim 14 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

20. A method as defined in claim 15 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

21. A method as defined in claim 16 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

22. A method as defined in claim 12 wherein controlling the solvent to hydrocarbon ratio comprises a step of initially increasing the solvent to hydrocarbon ratio by a predetermined increment, and
   (a) if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and
   (b) if the reaction rate and/or reactivity moves away from the desired reaction rate and/or reactivity range, lowering the solvent to hydrocarbon ratio, and if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

23. A method as defined in claim 12 wherein controlling the solvent to hydrocarbon ratio comprises a step of initially decreasing the solvent to hydrocarbon ratio by a predetermined increment, and
   (a) if the reaction rate and/or reactivity moves toward the desired reaction rate and/or reactivity range, continuing to decrease the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range; and
   (b) if the reaction rate and/or reactivity moves away from the desired reaction rate and/or reactivity range, increasing the solvent to hydrocarbon ratio, and if the reaction rate and/or reactivity moves toward the desired reaction rate and/or reactivity range, continuing to increase the solvent to hydrocarbon ratio to a point that the reaction rate and/or reactivity falls within said desired reaction rate and/or reactivity range or to a point that the reaction rate and/or reactivity does not move further toward the desired reaction rate and/or reactivity range.

24. A method as defined in claim 12 wherein, if the reaction rate and/or reactivity is within the desired reaction rate and/or reactivity range, maintaining the solvent to hydrocarbon ratio substantially at its initial value.

25. A method as defined in claim 12 wherein
   the hydrocarbon comprises a compound selected from a group consisting of cyclohexane, cyclohexanone, cyclohexanol, cyclohexylhydroperoxide, o-xylene, m-xylene, and p-xylene;
   the oxidant comprises oxygen; and
   a major portion of the acid comprises a compound selected from a group consisting of adipic acid, phthalic acid, isophthalic acid, and terephthalic acid.

26. A method as defined in claim 12 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

27. A method as defined in claim 22 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

28. A method as defined in claim 23 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

29. A method as defined in claim 24 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

30. A method as defined in claim 25 wherein the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

* * * * *

UNITED STATES PATENT AND TRADEMARK OFFICE
CERTIFICATE OF CORRECTION

| | |
|---|---|
| PATENT NO. | : 6,037,491 |
| APPLICATION NO. | : 08/900323 |
| DATED | : March 14, 2000 |
| INVENTOR(S) | : Eustathios Vassiliou et al. |

It is certified that error appears in the above-identified patent and that said Letters Patent is hereby corrected as shown below:

Claim 1, column 14, line 35, "the method being characterized by" should read --the method being continuous and characterized by--.
Claim 1, column 14, lines 38 and 39, "first temperature" (both instances) should read --reaction temperature-- (both instances).
Claim 1, column 14, line 43, "first temperature" should read --reaction temperature--.
Claim 11, column 16, line 14, "the oxidation" should read --the continuous oxidation--.
Claim 11, column 16, lines 24 and 25, "first temperature" (both instances) should read --reaction temperature-- (both instances).
Claim 11, column 16, line 28, "first temperature" should read --reaction temperature--.

Signed and Sealed this

Seventeenth Day of July, 2007

JON W. DUDAS
*Director of the United States Patent and Trademark Office*